US00PP34687P2

(12) United States Plant Patent
Whitcomb

(10) Patent No.: US PP34,687 P2
(45) Date of Patent: Oct. 25, 2022

(54) SOUTHERN WAX MYRTLE OR BAYBERRY PLANT NAMED 'WHIT XXIX'

(50) Latin Name: *Myrica cerifera*
Varietal Denomination: Whit XXIX

(71) Applicant: Lacebark, Inc., Stillwater, OK (US)

(72) Inventor: Carl E. Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 0 days.

(21) Appl. No.: 17/803,272

(22) Filed: Apr. 18, 2022

(51) Int. Cl.
*A01H 5/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

| | | | |
|---|---|---|---|
| PP6,411 | P | 11/1988 | Craven, III |
| PP7,555 | P | 6/1991 | Bracken |
| PP18,731 | P2 | 4/2008 | McCracken |
| PP19,789 | P2 | 3/2009 | Barrett |

*Primary Examiner* — Annette H Para
(74) *Attorney, Agent, or Firm* — Jeffrey L. Streets; Streets Lawfirm

(57) ABSTRACT

A new and distinct variety of southern wax myrtle, *Myrica cerifera*, which has been given the cultivar name 'Whit XXIX' is characterized by an upright growth habit with dense evergreen foliage which is aromatic and resistant to damage by white tail deer and tolerant to cold down to −18 F. Foliage is dense, with the many broad flat leaves making it effective as a visual barrier as well as noise reduction. The new cultivar 'Whit XXIX' has more dense branching and more leaves compared to other plants of similar size and age, with branches primarily produced on the second (summer) flush.

4 Drawing Sheets

Latin name: *Myrica cerifera.*
Varietal denomination: 'Whit XXIX'.

BACKGROUND OF THE INVENTION

Field of the Invention

The present invention relates to a new and distinct variety or cultivar of the native evergreen shrub, *Myrica cerifera*, commonly known as Southern Wax Myrtle.

Description of the Related Art

Southern wax myrtle is a small, aromatic, evergreen shrub or small tree. Native populations exist from east Texas across the south and northward to New Jersey. Seedlings typically grow 8 to 12 feet tall with an occasional plant reaching 20 feet. Wax myrtle grow well in sun or shade and in a wide range of soils, from marginally drained stream banks to deep sands and clay, plus are very drought tolerant. Contributing to this wide adaptability is the root association with the nitrogen fixing bacterium, *Frankia alni*. The bacterium is able to take nitrogen from air and convert it to nitrate, which allows this and others in the genus to grow on very marginal soils. In native coastal regions, wax myrtle can be weedy due to the large quantity of seeds produced. The seed dispersal is mostly by numerous bird species especially quail and turkey.

Wax myrtle is effective as a hedge or screen in reducing noise from adjacent areas. For example, in 1973, Whitcomb and Stowers studied the effectiveness of a number of species as hedges using a sound generator, lawn mower and automobile. They found that a broadleaved evergreen hedge was most efficient giving a 5 to 7 decibel reduction in sound 10 or 20 feet behind the hedge. In the study, width of the hedge was less important than leaf characteristics, particularly with low frequency sounds. A reduction of 5 decibels amounts to a reduction of about 50% in the apparent loudness of a sound. The new wax myrtle, 'Whit XXIX' has particularly dense foliage which would enhance effectiveness as a noise reducer.

The breeding/selection program with southern wax myrtle began in 1988. Initial seeds for the study were collected in the Appalachian Mountains in northwestern Virginia at or near the northern limit of the native population. That same year, seeds were also collected from a native population near Birmingham, Ala. Seedlings from those collections were planted in fields near Stillwater, Okla. The objective was an evaluation of tolerance to cold, drought, drying winds and heavy clay soils in the northern part of hardiness zone 7. When seedlings were four years old, a cold level of −2 F killed all seedlings from Alabama but did not harm seedlings from Virginia. During the succeeding years and 8 generations [consistently selecting the best seedlings for parents for the next generation, seeds were saved from the most cold-tolerant seedlings with darkest foliage and planted in open fields for evaluation. In 2015, seedlings from a selected parent showing promise and were planted in the field. From this seedling population there were 32 seedlings. During a period in February 2021, temperatures dropped to −1, then −18, then −6 F. By March, many seedlings were dead, while others had lost most of their leaves but recovered with spring growth. One seedling showed no damage or leaf discoloration in March and had the same appearance as the previous November. This seedling was selected for further evaluation and has been given the cultivar name 'Whit XXIX'.

U.S. Plant Pat. No. 7,555, by Brackin claims a wax myrtle with deeply serrated leaves with a yellow-green mid-rib and resistance to leaf spot disease and cold hardy to −4 F.

U.S. Plant Pat. No. 6,411, by Craven claims a wax myrtle with compact growth with a broad spreading, suckering mounded growth habit, light yellow-green leaves that mature to dark olive green and cold hardy to 0 F.

U.S. Plant Pat. No. 18,731 by McCracken claims a wax myrtle plant with densely branched brilliant yellow foliage, with no mention of cold tolerance.

U.S. Plant Pat. No. 19,789 by Barrett claims a wax myrtle with compact upright, globular growth habit, and grows well between +32 F and +85 F, but no mention of tolerance to cold.

Southern wax myrtle are reportedly resistant to damage by grazing or rubbing by white tail deer, likely due to volatile oils from leaves and stems. With a high population of white tail deer in central Oklahoma, no deer damage has occurred to any of the seedlings grown during the 30+ years of this study.

BRIEF SUMMARY OF THE INVENTION

The plant of the present invention is a new and distinct variety of southern wax myrtle, *Myrica cerifera*, which has been given the cultivar name 'Whit XXIX'. It is characterized by an upright growth habit with dense evergreen foliage which is aromatic and resistant to damage by white tail deer and tolerant to cold down to −18 F. Foliage is dense, with the many broad flat leaves making it effective as a visual barrier as well as noise reduction.

Visual observation suggested more dense branching and more leaves on 'Whit XXIX' compared to other plants of similar size and age. To differentiate and document differences in foliage and branching characteristics between the new variety, 'Whit XXIX' and other seedlings growing in adjacent rows from the same parent population or previous populations from other parents, comparisons of six-inch lengths of stems were evaluated for number of leaves on eight stems on a plant with the first flush (spring growth) and second (summer flush). The number of leaves on first flush from eight branches on 'Whit XXIX' averaged 34.1. The number of leaves from eight branches on six other plants of similar size and age averaged 28.1, 20.2, 19.5, 20.9, 15.5 and 16.4. There were few branches on any of the first flush branches on any of the plants evaluated. With the seed populations grown and evaluated during the 30+ years of this research, branches are primarily produced on the second/summer flush.

The number of developing branches per six-inch section of second/summer flush of 'Whit XXIX' on 8 branches counted averaged 21.1. The number of branches on various other wax myrtle plants of similar size and age and with 8 branches counted on each plant averaged 10.75, 7.6, 11.9, 12.4, 14.1 and 9.8.

DETAILED BOTANICAL DESCRIPTION

Figure 1:
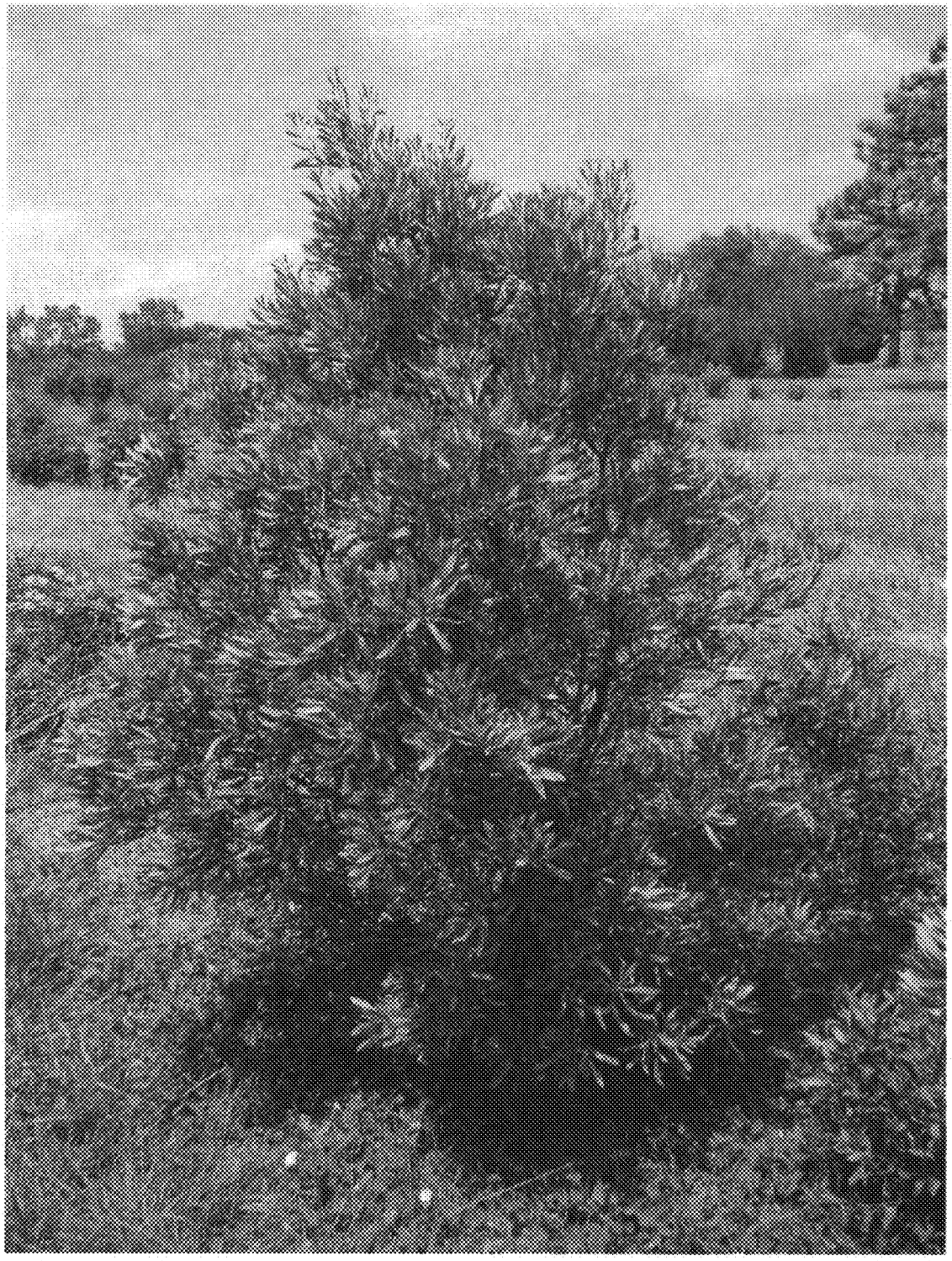
FIG. 1 is a full color view of the new and distinct variety of southern wax myrtle plant named 'Whit XXIX' showing foliage color and density at age seven years. Appearance of wax myrtle plant 'Whit XXIX' as photographed in March 2021 following a winter cold temperature period in February of −1, −18, and −6 F.
Figure 2:
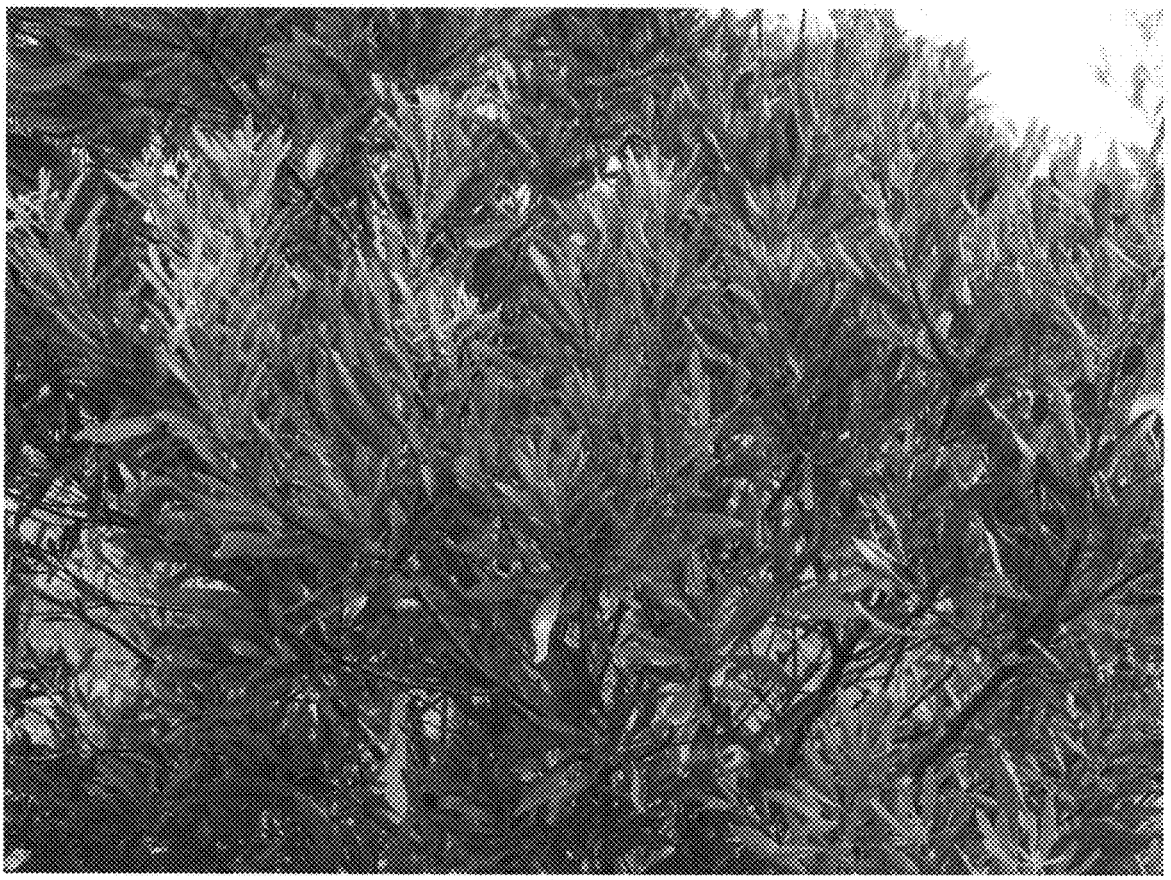
FIG. 2 is a full color view of the new and distinct variety of southern wax myrtle plant named 'Whit XXIX' showing slightly more dense foliage than plants of similar age and size and growing under similar field conditions.
Figure 3:
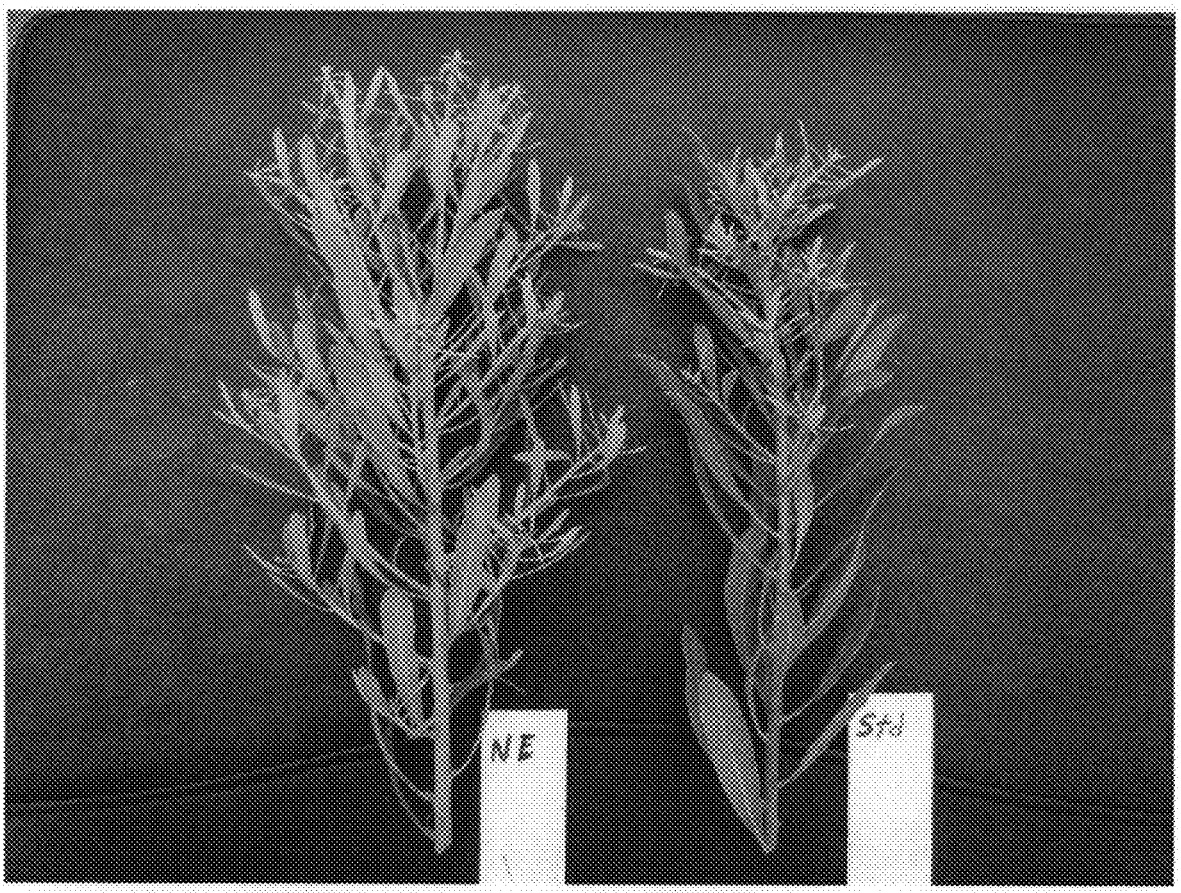
FIG. 3 is a full color view of the new and distinct variety of southern wax myrtle plant named 'Whit XXIX' showing a much greater number of branches produced during summer flush compared to plants of similar age and size and growing under similar field conditions.
Figure 4:
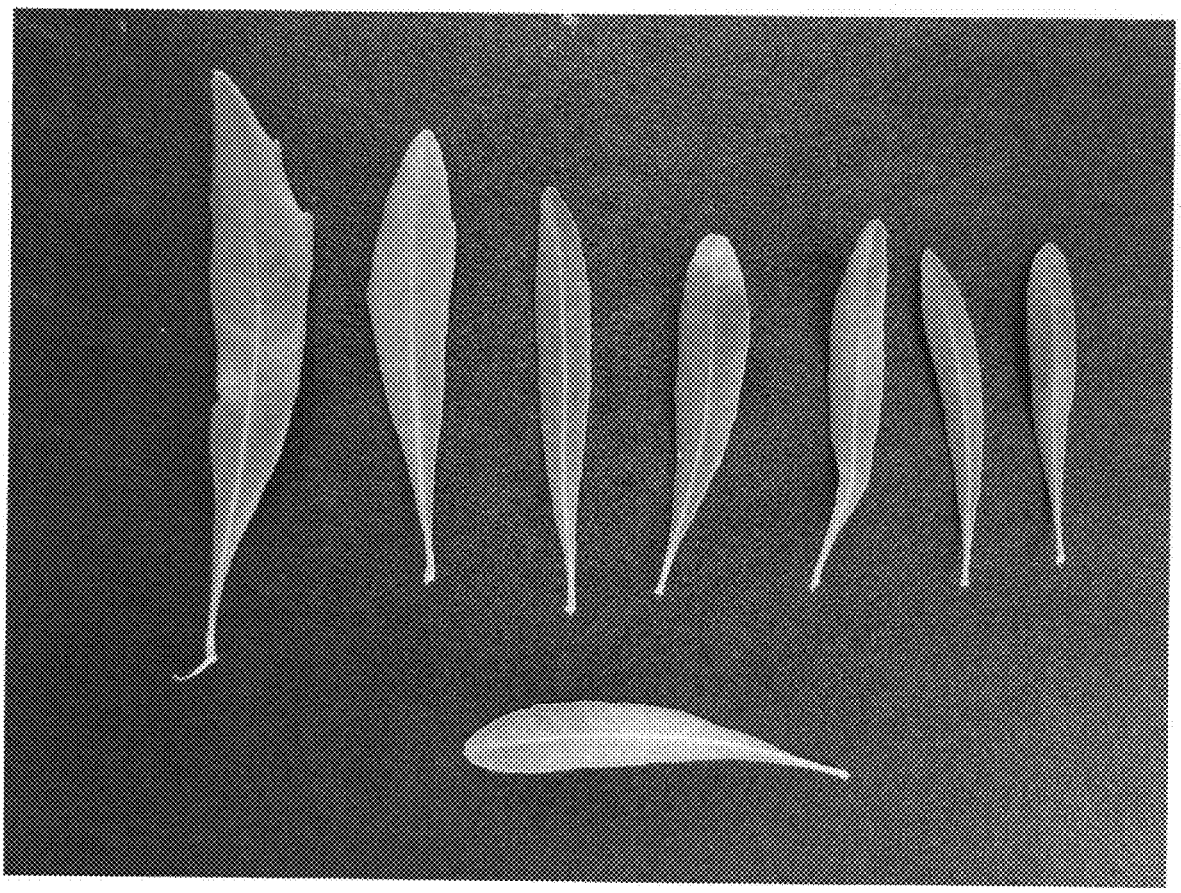
FIG. 4 is a full color view of leaves from summer growth of the new and distinct variety of southern wax myrtle named 'Whit XXIX' showing largest leaves at the base of the stem progressing to smallest leaves at the tip.

The following is a botanical description of the new and distinct variety of southern wax myrtle, *Myrica cerifera* which has been given the cultivar name 'Whit XXIX'. Specific color designations set forth by number designation are in accordance with The Royal Horticultural Society Colour Chart (1966). General color recitations are consistent with ordinary American color terminology.

The plant was 7 years old and was grown outdoors in an open field of sandy, clay loam near Stillwater, Okla. Drip irrigation was applied for the first two years, but in years 3 to 7, no drip was applied in order to evaluate drought tolerance. No signs of drought stress were observed.

The plant:

*Type*.—Broadleaf evergreen shrub or small tree.

*Classification*.—Southern wax myrtle, *Myrica cerifera*.

*Growth habit*.—Upright growing plant with dense foliage, typically with a single stem and no secondary branches or suckers near the base.

*Origin*.—Selected from a population of seedlings resulting from a seedling selection process begun in 1988 with seeds from northern Virginia and progressing through eight generations to the seedlings planted in 2015 resulting in 'Whit XXIX' cultivar.

*Propagation*.—The new cultivar 'WHIT XXIX' has been propagated by softwood to early semi hardwood cuttings of current season's growth taken in spring and placed under intermittent mist in a greenhouse near Stillwater, Okla. Distinguishing characteristics of the resulting plants remain identical to the parent through succeeding asexual propagations.

*Hardiness*.—The new and distinct cultivar of southern wax myrtle named 'Whit XXIX' is exceptionally cold hardy having no injury from severe winter temperatures of −1, −18 and −6 F during a period in February 2021.

*Pests and disease*.—Resistant to grazing and rubbing by white tailed deer, even under high deer population. Foliage damage may occur from fall webworms and bagworms. No leaf spot disease has been observed on any of the seedling grown during this study.

The flowers:

*Flowering period*.—No flowers of either sex have been observed on the new wax myrtle named 'Whit XXIX' which is seven years old. Wax myrtle are dioecious with a typical ratio of about 1 male to 3 females. Typically, among wax myrtle seedlings grown during the 30+ years of this study, the wax myrtle begin flowering at age three years old.

The foliage:

*The foliage and form*.—Growth is upright with dense branching and foliage. Old leaves remain on the plant after new spring growth and slowly drop during the growing season as new growth reduces light below the compensation point.

*Leaf arrangement*.—Alternate and simple, spaced variably around the stem and with variable distances between leaves.

*Leaf shape*.—Oblanceolate, tapering in width variably from about the center to the base with length variable, but generally cuneate above a short stout petiole of variable length. Leaves at the base of the flush of growth are larger and become progressively smaller transitioning to the tip. Leaf tips are variable, obtuse to acute. Leaves near the base typically have from one to five or more serrations, primarily near the tip but with variations in placement while leaves further up the stem typically have no serrations.

*Leaf surface and color*.—Glabrous, with color variable, among leaves on a stem of current season's growth, but mature leaves are about 146 A or B or 148 A on the upper surface (best match, but not a good fit as leaves are darker) and about 152 A or B on lower surface. New emerging growth is about 152 B, C or D on the upper surface, transitioning to 152 A then 146 A or B or 148 A.

*Leaf texture*.—Upper and lower surfaces, smooth, glabrous, leathery. Upper surface with a glossy luster, while lower surface is dull.

*Leaf size*.—Variable, ranging from about 1.5 to 4 inches with the longest leaves at the base of a season's flush of growth and with decreasing size transitioning to the tip.

The branches and bark:

*Branch color*.—Current season's stem between about 152 B or C, early, transitioning to 166 B or C and fully developed branches about 166 A.

*Bark*.—Grey to grayish green smooth, color about 164 A or B, but no good fit among the color choices.

I claim:

1. A new and distinct variety of *Myrica cerifera* plant named 'Whit XXIX', substantially as illustrated and described herein having dense branching and dense dark foliage and tolerance to cold to −18 F.

* * * * *